(12) United States Patent
Heisig et al.

(10) Patent No.: US 10,786,202 B2
(45) Date of Patent: Sep. 29, 2020

(54) QUANTIFYING GRIP STRENGTH AND CHARACTERIZING MOVEMENT IDIOMS

(71) Applicant: International Business Machines Corporation, Armonk, NY (US)

(72) Inventors: Stephen J. Heisig, Tarrytown, NY (US); Katsuyuki Sakuma, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 184 days.

(21) Appl. No.: 15/410,836

(22) Filed: Jan. 20, 2017

(65) Prior Publication Data

US 2018/0085061 A1 Mar. 29, 2018

Related U.S. Application Data

(60) Provisional application No. 62/401,117, filed on Sep. 28, 2016.

(51) Int. Cl.
*A61B 5/00* (2006.01)
*G01B 7/16* (2006.01)
(Continued)

(52) U.S. Cl.
CPC .......... *A61B 5/6826* (2013.01); *A61B 5/1077* (2013.01); *A61B 5/1125* (2013.01);
(Continued)

(58) Field of Classification Search
CPC ....... A61B 5/40; A61B 5/1125; A61B 5/4082; A61B 5/4076; A61B 5/44; A61B 5/449; A61B 5/45; A61B 5/4519; A61B 5/4538; A61B 5/4842; A61B 5/68; A61B 5/6801; A61B 5/6826; A61B 5/6832; A61B 5/103;
(Continued)

(56) References Cited

U.S. PATENT DOCUMENTS

| 3,154,067 | A | 10/1964 | Stenstrom | |
| 6,360,615 | B1 * | 3/2002 | Smela | A61B 5/1124 73/862.474 |

(Continued)

OTHER PUBLICATIONS

Sakai et al., Strain in the nail at fingertip compression, 2007, 13: 449-452, Skin Research and Technology. ProQuest [online]: British Library Document Supply Centre Inside Serials & Conference Proceedings [retrieved on Aug. 16, 2018]. Retrieved from: Academic Search Complete. DOI: 10.1111/j.1600-0846.2007.00250.x. (AN: 26851343).*

(Continued)

*Primary Examiner* — Matthew Kremer
*Assistant Examiner* — Avery M Foley
(74) *Attorney, Agent, or Firm* — L. Jeffrey Kelly; Otterstedt, Wallace & Kammer, LLP

(57) ABSTRACT

A sensor includes a bridge circuit including one or more strain gauges mounted on a nail plate, the bridge circuit outputting a voltage signal, an amplifier circuit amplifying the voltage signal output by the bridge circuit to generate an amplified signal, an analog-to-digital (A/D) converter converting the amplified signal into a digital signal, a controller receiving the digital signal and facilitating communication with a receiver, and an antenna configured to transmit the digital signal.

10 Claims, 10 Drawing Sheets

(51) Int. Cl.
*A61B 5/107* (2006.01)
*A61B 5/11* (2006.01)

(52) U.S. Cl.
CPC ............ *A61B 5/4082* (2013.01); *A61B 5/449* (2013.01); *A61B 5/4842* (2013.01); *G01B 7/18* (2013.01); *G01B 7/20* (2013.01); *A61B 2503/40* (2013.01); *A61B 2562/0261* (2013.01)

(58) Field of Classification Search
CPC ......... A61B 5/107; A61B 5/1077; A61B 5/11; A61B 5/1107; G01B 7/16; G01B 7/18; G01B 7/20
See application file for complete search history.

(56) References Cited

U.S. PATENT DOCUMENTS

| | | | |
|---|---|---|---|
| 9,238,142 | B2 | 1/2016 | Heldman |
| 9,282,928 | B1 | 3/2016 | Giffrida |
| 9,302,046 | B1 | 4/2016 | Giffrida |
| 9,314,190 | B1 | 4/2016 | Giffrida |
| 2002/0139203 | A1* | 10/2002 | Chimura ............ G01G 3/1412 73/862.627 |
| 2006/0149167 | A1 | 7/2006 | Yeh et al. |
| 2007/0228500 | A1* | 10/2007 | Shimazu ................. G01B 7/18 257/417 |
| 2010/0331738 | A1* | 12/2010 | Stein ...................... A61B 5/103 600/587 |
| 2011/0208444 | A1* | 8/2011 | Solinsky ................ A61B 5/112 702/41 |
| 2011/0267042 | A1* | 11/2011 | Sano .................... A61B 5/1125 324/207.11 |
| 2013/0291653 | A1* | 11/2013 | Kempainen ............. G01L 5/161 73/862.045 |
| 2015/0164377 | A1 | 6/2015 | Nathan et al. |
| 2015/0332004 | A1 | 11/2015 | Najafi |
| 2015/0380355 | A1* | 12/2015 | Rogers .................. H01L 23/538 257/773 |
| 2016/0038080 | A1 | 2/2016 | Moreno |
| 2016/0100776 | A1 | 4/2016 | Najafi |
| 2016/0303110 | A1 | 10/2016 | Shah |
| 2017/0075465 | A1* | 3/2017 | Pedder .................. G06F 3/0414 |
| 2017/0251956 | A1 | 9/2017 | Kandori et al. |

OTHER PUBLICATIONS

Sensor Interface PCD-300B. Hardware Instruction Manual [online]. Kyowa Electronic Instruments Co., Ltd., 2008 [retrieved on Sep. 18, 2018]. Retrieved from the internet: <URL: https://www.kyowa-ei.com/eng/download/support/download/manual/s_pcd-300_series_manual_im-a-691c_01_eng.pdf>.*

Mascaro, S. A. et. al., "Photoplethysmograph fingernail sensors for measuring finger forces without haptic obstruction", IEEE Transactions on Robotics and Automation, 17(5), Oct. 2001, pp. 698-708. DOI: 10.1109/70.964669.

Mascaro, S. A. et. al.,"Understanding of fingernail-bone interaction and fingertip hemodynamics for fingernail sensor design," Haptics. IEEE, Feb. 2002, pp. 1-8.

Kao, Hsin-Liu et. al. "NailO: Fingernails as an Input Surface," CHI 2015, Apr. 18-23, 2015, pp. 1-5, Seoul, Republic of Korea.

Tandon, Utkarsh, https://www.kickstarter.com/projects/815665829/onering-an-intelligent-monitoring-device-for-parki/description, Jan. 2016, pp. 1-12.

Moreno, Manuel V., http://www.sense4care.com/en/about-us/parkinson, Dec. 2015, pp. 1-4.

Stephen J Heisig et al., unpublished U.S. Appl. No. 15/856,435, filed Dec. 27, 2017, Title, pp. 1-22 plus 10 sheets of drawings.

Paul J. Otterstedt, List of IBM Patents or Patent Applications Treated as Related, Jun. 25, 2018, pp. 1-2.

Tamakil, Emi et al. "Gesturenail: Wireless Hand Gesture System", International Journal of Computer Science, Engineering and Applications (IJCSEA) vol. 3, No. 5, Oct. 2013 (Year: 2013) pp. 29-38.

* cited by examiner

US 10,786,202 B2

QUANTIFYING GRIP STRENGTH AND CHARACTERIZING MOVEMENT IDIOMS

CROSS-REFERENCE TO RELATED APPLICATIONS

This application claims the benefit of U.S. Provisional Patent Application No. 62/401,117 filed on Sep. 28, 2016, the complete disclosure of which is expressly incorporated by reference herein in its entirety for all purposes.

BACKGROUND

The present disclosure relates generally to quantifying grip strength and characterizing movement idioms based on fingernail deformation. These two functions are useful for evaluating subjects with degenerative neurological diseases or other conditions such as cardiovascular disease or sarcopenia where grip strength fluctuates in relation to disease state. They also enable a new type of human computer interface.

Patients with a degenerative neurological disease, like Parkinson's disease (PD), suffer from a diverse set of symptoms. The hallmark motor symptoms of Parkinson's disease are tremor, bradykinesia, rigidity, and postural instability. These symptoms change the way a patient moves and how they interact with objects in daily life.

In evaluating the effect of a Parkinson therapy, one problem is to categorize a patient's current status as 'ON' meaning relatively able to function given their current disease state, 'OFF' meaning not functioning well or actually being rigid or paralyzed, and 'ON with complications' meaning able to move but with extra movement problems (typically dyskinesias or dystonia). Patients with more 'ON' time with a new therapy relative to the previous therapy are considered to have benefitted.

For Parkinson's patients the burden of their disease is considerable, and the burden of medication is considerable so it is desirable not to add a burden of monitoring. For a population with increasing cognitive deficits, depression, apathy, and mobility issues monitoring and testing regimes can become challenging. Existing methods of characterizing a patient's state, which involve consciously performing tasks requiring manual dexterity (e.g., operating a mobile phone app) add a burden of tracking to an already overwhelmed patient. Schemes requiring consistently positioning sensors accurately on different parts of their bodies also add to this burden and result in lower compliance levels. One last challenge to wearable monitoring is the condition of a patient's skin. Many Parkinson's patients are older, having thin, brittle (friable) skin. In cases where wearable patches must be applied and removed on a daily basis, tears and resulting infection or other problems can result.

BRIEF SUMMARY

According to an exemplary embodiment of the present invention, a system includes a sensor having a bridge circuit including one or more strain gauges mounted on a nail plate, the bridge circuit outputting a voltage signal, an amplifier circuit amplifying the voltage signal output by the bridge circuit to generate an amplified signal, an analog-to-digital (A/D) converter converting the amplified signal into a digital signal, a controller receiving the digital signal and facilitating communication with a receiver, and an antenna configured to transmit the digital signal.

According to an exemplary embodiment of the present invention, a method of characterizing grip strength and movement idioms to track disease state in a subject includes measuring, using a sensor, strain on a nail plate of a subject, wherein the sensor outputs a data stream corresponding to the measuring, communicating the data stream to a receiver, and interpreting, by the receiver, the data stream to determine a parameter of interest of the subject.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

enabling the capture of fine digit motions and forces transmitted through fingers and toes; and a nail mounted sensor that does not touch a subject's skin.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Figure 1:
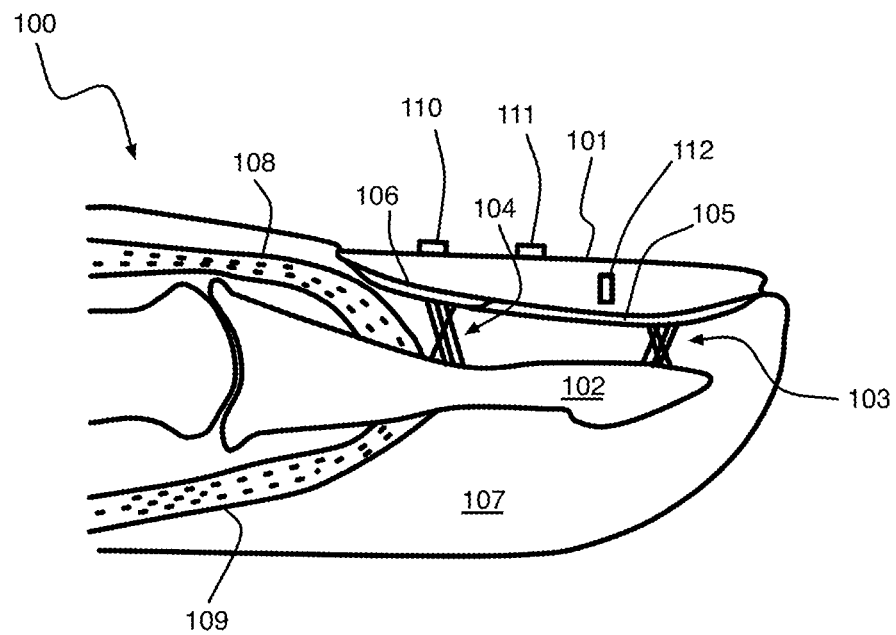
FIG. 1 is shows a longitudinal view of a distal finger area and mounted circuitry according to an embodiment of the present invention.

According to an embodiment of the present invention, a continuous data stream is collected that is interpreted by software to measure grip strength and characterize movement idioms. These measurements are correlated with disease state in patients, who may be limited in their ability to remember and perform explicit tasks, operate mobile phones, or wear sensors on their skin.

According to one or more embodiments of the present invention, a plurality of strain gauges with accompanying circuitry measure a deformation of an unguis (i.e., fingernail or toenail) in longitudinal and transverse directions, and to transmit this information wirelessly to a receiver such as a smartwatch or mobile phone.

It should be understood herein that the electrical conductance of a strain gauge (typically formed of a doped silicon or metal) varies with its geometry, such that a deformation of the strain gauge results in a change in its electrical resistance. The stress on a strain gauge can therefore be inferred from a measured resistance of the strain gauge using a known gauge factor, which is a ratio of relative change is resistance to the strain on the test piece. The resistance of the strain gauge can be measured using a Wheatstone bridge. Strain gauges measure strain that can be related to stress, force, torque and a host of other stimuli including displacement, acceleration and position.

According to one or more embodiments of the present invention, anatomical features of primate fingers and toes cause nails to deform in certain predictable ways under direct, longitudinal, and shear forces. According to an embodiment of the present invention, a strain gauge is mounted on a nail plate to measure this deformation, which is then used to estimate the force and direction causing the deformation. Flexion and extension of the fingers and toes also causes deformation of the nail plate, such that motion without touching an object can be characterized. A deformation data stream is used to estimate grip strength in the hands or pressure exerted by the toes (e.g., for balance).

According to one or more embodiments of the present invention, grip strength is characterized as a maximum grip force generated by a subject and the time it takes to develop the maximum strength. According to one or more embodiments of the present invention, the maximum and average grip strength, as well as number and speed of finger motions, is used to estimate a subject's fluidity versus rigidity, bradykinesia, and hand strength parameters. According to one or more embodiments of the present invention, using the data stream from the strain gauge, activities of daily living such as tying a necktie and buttoning/unbuttoning a shirt can be identified as an idiom and characterized and compared on a day to day basis. According to one or more embodiments of the present invention, characterized movements can include a subject making a pass-movement to identify themselves (similar to a password). According to one or more embodiments of the present invention, characterized movements can include specifying characters or letters by writing them on any surface with a finger appropriately configured with a sensor, or making gestures to control a computer such as scrolling, paging, selecting, or compressing files. Characteristics of motion idioms such as duration, force, and fluency can be used in determining a subject's state. In at least one embodiment of the present invention, parameters are used as proxies for the subject's ON, OFF state as part of a Parkinson's therapy.

Advantageously, embodiments of the present invention capture fine finger motions and forces transmitted through fingers and toes. Wearable actigraphy (i.e., non-invasive monitoring of rest/activity cycles) and inertial measurement unit (IMU) devices do not perform this function.

Advantageously, embodiments of the present invention of a nail mounted sensor do not require touching a subject's skin. If the normal rate of growth is taken as approximately 3 millimeters per month, a sensor bonded to a subject's nail plate would not need replacement for at least a month. Moreover, older patients typically exhibit slower rates, thus the time for replacement of the sensor is elongated. In the exemplary case of a clinical trial a new sensor can be bonded by a nail technician during each clinical visit. The sensor itself requires no attention or maintenance from the subject.

FIG. 1 shows a longitudinal view of a distal finger area 100. The nail plate 101 is anchored to the distal phalangeal bone 102 by the anterior and posterior ligaments 103 and 104, respectively, the nail bed 105 and the nail matrix 106. FIG. 1 further shows the deformable pulp 107, and extensor and flexor tendons, 108 and 109, respectively.

Figure 2:
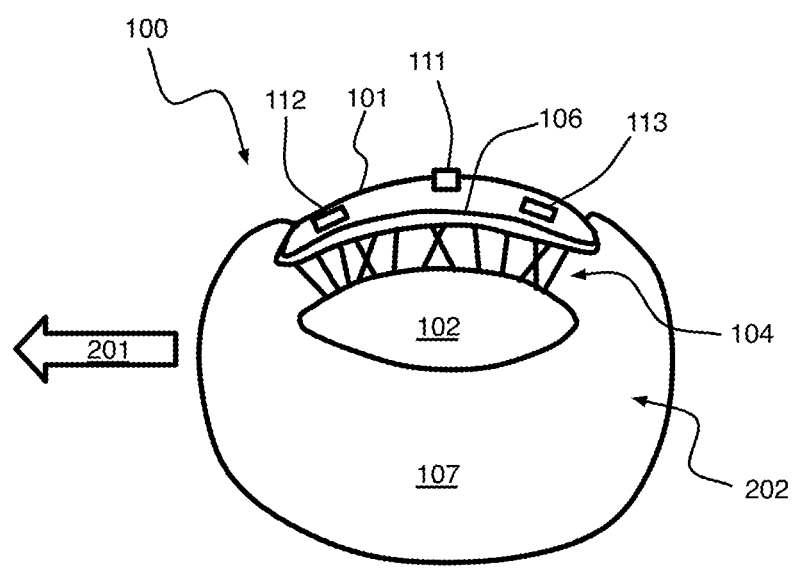
FIG. 2 is shows a transverse view of a distal finger area and mounted circuitry according to an embodiment of the present invention.

FIG. 2 is a transverse view of the distal finger area 100. Again, the nail plate 101 is anchored to the distal phalangeal bone 102 by the anterior ligaments (not shown) and posterior ligaments 104, and the nail matrix 106.

Figure 3:
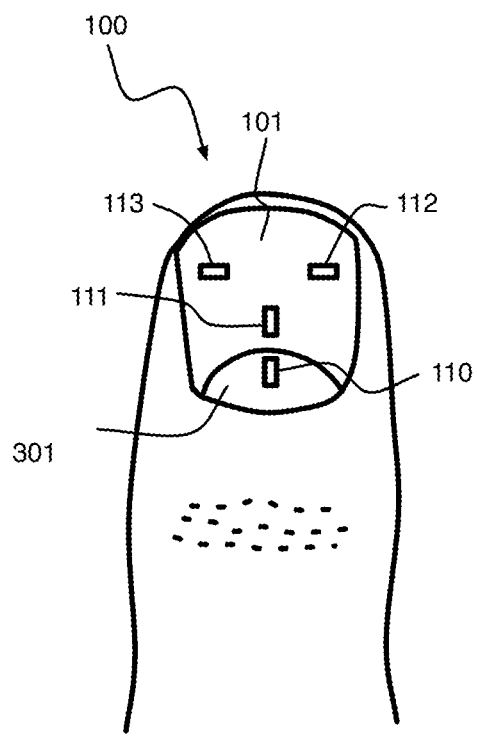
FIG. 3 is shows a dorsal view of a distal finger area and mounted circuitry according to an embodiment of the present invention.

FIG. 3 is a dorsal view of the distal finger area 100, including the nail plate 101 and lunula 301 (i.e., the visible part of the root of the nail). In at least one embodiment of the present invention, each strain gauge is connected to a respective Wheatstone bridge circuit. FIG. 3 shows a configuration of four strain gauges 110-113. It should be understood that the system can include a different number of strain gauges disposed at different locations.

According to one or more embodiments of the present invention, FIGS. 1-3 show combinations of strain gauges 110-113 disposed on the nail plate 101/lunula 301. The strain gauges 110-113 are connected to circuitry (see for example, FIGS. 4, 6A-C, and 7-14) configured to measure a piezoelectric effect generated by one or more of the strain gauges 110-113 and to transmit a signal via a wireless network, such as by Bluetooth, a Near Field Communication (NFC) or a Body Area Network (BAN), to a receiver (see FIG. 5), such as smart-ring, smartwatch, or mobile phone. According to one or more embodiments of the present invention, the strain gauges 110-113 are bonded (e.g., by an adhesive) to the top of the nail plate 101/lunula 301, where the strain gauges 110-113 are disposed at each margin of the nail (i.e., four strain gauges). The strain gauges 110-113 detect deformation depending on how the finger is pressed or moved against an object.

Direct Force Detection:

Referring to FIG. 2, when the finger is pressed directly downwards against an object the deformable pulp in the fingertip pushes on the lateral parts of the nail and makes it less convex since the center portion is anchored to the bone and is not free to move. This is deformation in the transverse direction and is proportional to the force exerted on the object. According to one or more embodiments of the present invention, the strain gauges measure deformation and the time taken to develop maximum deformation.

Left and Right Shear (Transverse) Forces:

If the finger is pressed against an object and moved leftward or rightward the deformable pulp 107 shifts to the following side and transverse nail plate deformation is more pronounced on that side. For example, with a rightward movement 201 (from the subject's point of view), the following side, i.e., 202 and transverse nail plate deformation is more pronounced on that side and would be sensed by strain gauge 113 as compared to strain gauge 112.

Positive and Negative Longitudinal Forces:

If the finger is pressed directly against an object and moved positively or negatively in the longitudinal direction the nail plate 101 will arch or bow, respectively. Similarly, if the tip of the finger is pressed into an object.

Extension and flexion of the fingertip also produces a deformation of the nail plate 101. Extension and flexion of the finger generated by the extensor and flexor tendons causes the nail plate 101 to bow or arch, respectively. That is, finger movement, without contacting an object, generates deformation that can be measured by the strain gauges.

According to one or more embodiments of the present invention, the system can be implemented as a Unified Parkinson's Disease Rating Scale (UPDRS) item used in daily neurological examinations. In this case, bradykinesia and disturbances of rhythm formation occurring in PD subjects can be assessed using a finger-tapping test. The evaluation of bradykinesia and disturbances of rhythm formation includes velocity, amplitude, and rhythm parameters. Conventional techniques relied on subject observation of these parameters.

Figure 4:
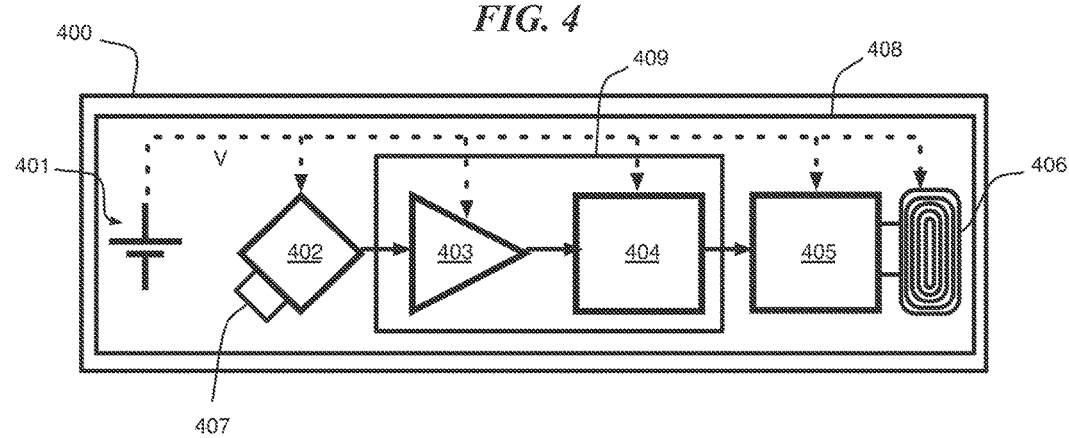
FIG. 4 is a block diagram of a sensor according to an embodiment of the present invention.
Figure 5:
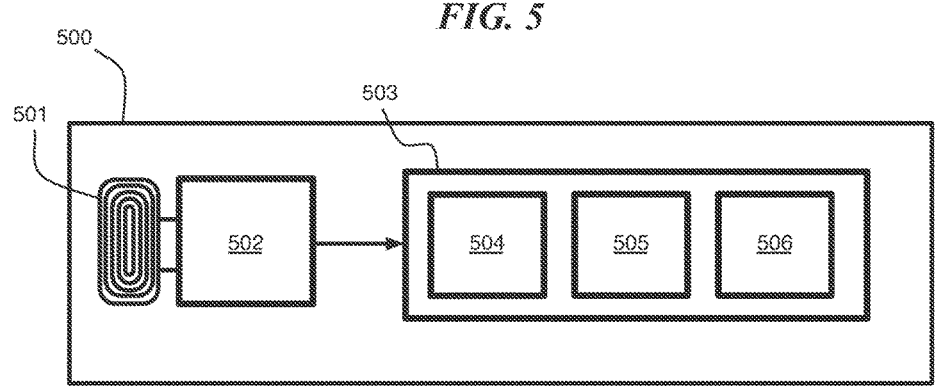
FIG. 5 is a block diagram of a receiver according to an embodiment of the present invention.

According to one or more embodiments of the present invention, FIGS. 4 and 5 show a sensor 400 and a receiver 500. According to one or more embodiments of the present invention, the sensor 400 comprises a power supply 401, bridge circuit 402, an amplifier circuit 403, analog-to-digital (A/D) converter 404, a communications controller 405 (e.g., an NFC controller, Bluetooth controller, etc.), and an antenna 406. The bridge circuit 402 connects one or more strain gauges, e.g., 407. It should be understood that receiver 500 can, in one or more embodiments of the present invention, be configured as a transmitter for communicating with the sensor 400. For example receiver 500 can send start/stop signal to a sensor 400 by using NFC.

According to one or more embodiments of the present invention, the sensor 400 comprises the power supply 401 providing a voltage V to the components of the sensor 400, the bridge circuit 402 including one or more strain gauges mounted on a nail plate, the bridge circuit 402 outputting a voltage signal, the amplifier circuit 403 amplifying the voltage signal output by the bridge circuit 402 to generate an amplified signal, the analog-to-digital (A/D) converter 404 converting the amplified signal into a digital signal, the communications controller 405 receiving the digital signal and facilitating communication with a receiver 500, and the antenna 406 configured to transmit the digital signal. According to one or more embodiments of the present invention, the communications controller 405 controls input signals corresponding to strain information and transmits the input signals to the receiver 500, external to the sensor 400.

Figure 6A:
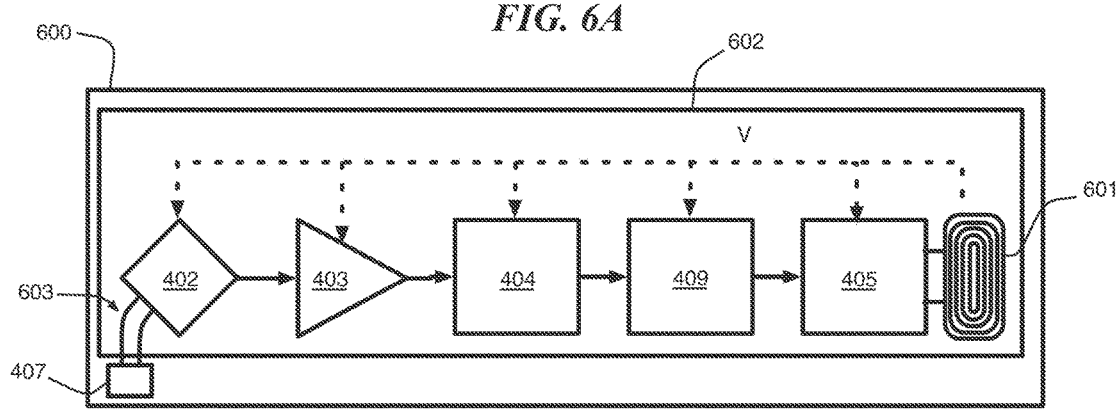
FIGS. 6A-C are diagrams of a sensor having a wireless power supply according to an embodiment of the present invention.

According to an embodiment of the present invention, the sensor 400 includes a micro-controller 409. According to one or more embodiments of the present invention, the functions of the amplifier 403 and the A/D converter 404 are implemented by software, which is executed by the micro controller 409 (e.g., a processor) as illustrated by FIG. 4. In at least one embodiment, the micro controller 409 bridges data communication between different components of the system. According to at least one embodiment of the present invention, the amplifier 403 and the A/D converter 404 are implemented as hardware, and the micro controller 409 is disposed between the A/D converter 404 and the communications controller 405 as illustrated in FIG. 6A, wherein the micro controller 409 prepares (e.g., conditions, buffers, etc.) the signal for the communications controller 405.

According to one or more embodiments of the present invention, the receiver 500 comprises an antenna 501, a communications controller 502 and a processing unit 503. The processing unit 503 comprises a processor 504, a storage medium 505 and a display 506. The sensor 400 and the receiver 500 support wireless network such as Bluetooth and/or NFC and/or BAN. According to one or more embodiments of the present invention, the receiver 400 executes signal processing software running on the processor 504 that interprets a signal received from a sensor 400 and estimates parameters including for example, force, direction, and gesture for each input (e.g., stress on the nail plate).

According to at least one embodiment of the present invention, an electromagnetic field generated by the receiver 500 supplies power to the sensor 400, e.g., during a recharge operation recharging the power supply 401. According to at least one embodiment of the present invention, the sensor 400 is configured to communicate data to the receiver 500. According to at least one embodiment of the present invention, the data communication between the sensor 400 and the receiver 500 is bidirectional.

According to at least one embodiment of the present invention, the receive 500 can be embodied as a computer system including a desktop computer, cloud based server, a wearable computing device, such as a smart watch or disposed in a footwear (e.g., in a sole of a shoe near to a sensor disposed on a toenail), and the like.

According to an exemplary embodiment of the present invention, the power supply 401 is a battery (e.g., a lithium ion battery), wireless power transfer circuitry, or the like.

According to an exemplary embodiment of the present invention, a sensor 600 (FIG. 6A) having a wireless power supply. The sensor 600 includes an antenna 601 (e.g., NFC antenna) converting a signal (e.g., an oscillating magnetic field) received from the receiver side into an electric current. The antenna 601, which in at least one embodiment is formed as a coil, provides a voltage V to the components of the sensor 600, including a bridge circuit 402 having a stain gauge 407, an amplifier circuit 403, an analog-to-digital (A/D) converter 404 and a communications controller 405. Thus, the antenna 601 performs a wireless power transfer function.

According to be exemplary embodiment of the present invention, each strain gauge is connected to individual a bridge circuit 402 (e.g., a Wheatstone bridge circuit, half-bridge circuit), wherein each strain gauge generates an output signal. One or more strain gauges can be connected to the same bridge circuit, for example, for temperature compensation, to cancel a thermal effect of lead wires, to reduce the number of Wheatstone bridge circuit, etc.

Figure 6B:
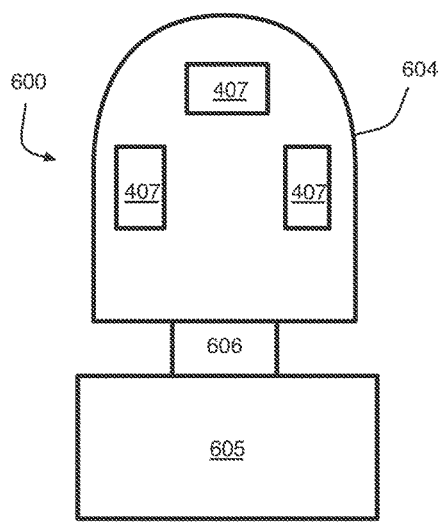
Figure 6C:
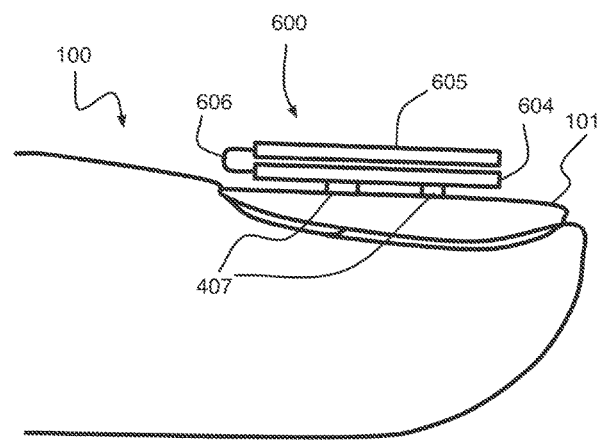

According to an exemplary embodiment of the present invention, the amplifier circuit 403, analog-to-digital (A/D) converter 404, communications controller 405 and antenna 406 are mounted to a printed circuit board 602 (see FIG. 6A) of the sensor 600, together with a first portion of the bridge circuit 402, wherein a second portion of the bridge circuit including the strain gauge 407 is mounted to the nail plate of the subject, apart from the printed circuit board 602, and connected to the first portion of the bridge circuit 402 by wire leads 603. According to at least one embodiment of the present invention, the sensor 400 is formed on a flexible circuit board 408, including the strain gauge 407. According to still another exemplary embodiment, the sensor 400 is formed on a flexible circuit board, except for the strain gauge 407. It should be understood that various configurations of the sensor 400 can be envisioned in view of the present disclosure, and embodiments described herein are not limiting. For example, according to at least one exemplary embodiment and as depicted in FIGS. 6B and 6C, the strain gauges 407 are mounted on a flexible circuit board 604, which is connected to a second circuit board 605 (e.g., a printed circuit board or flexible circuit board). The second circuit board 605 includes one or more of a bridge circuit 402 excluding the strain gauges 407, an amplifier circuit 403, an analog-to-digital (A/D) converter 404, a communications controller 405, and an antenna 406, similar to the printed circuit board 602 shown in FIG. 6A. According to at least one embodiment of the present invention, the second circuit board 605 includes a power supply 401. According to at least one embodiment of the present invention, the flexible circuit board 604 and the second circuit board 605 are connected by a data communications bus 606, which is, for example, a wire or a tape wire. According to an exemplary embodiment of the present invention, the flexible circuit board 604 and the second circuit board 605 are stacked on other another, with the data communication bus interposed between the circuit boards. According to at least one embodiment, the flexible circuit board 604, the second circuit board 605 and the data communications bus 606 are formed as a unitary flexible circuit board.

Figure 7:
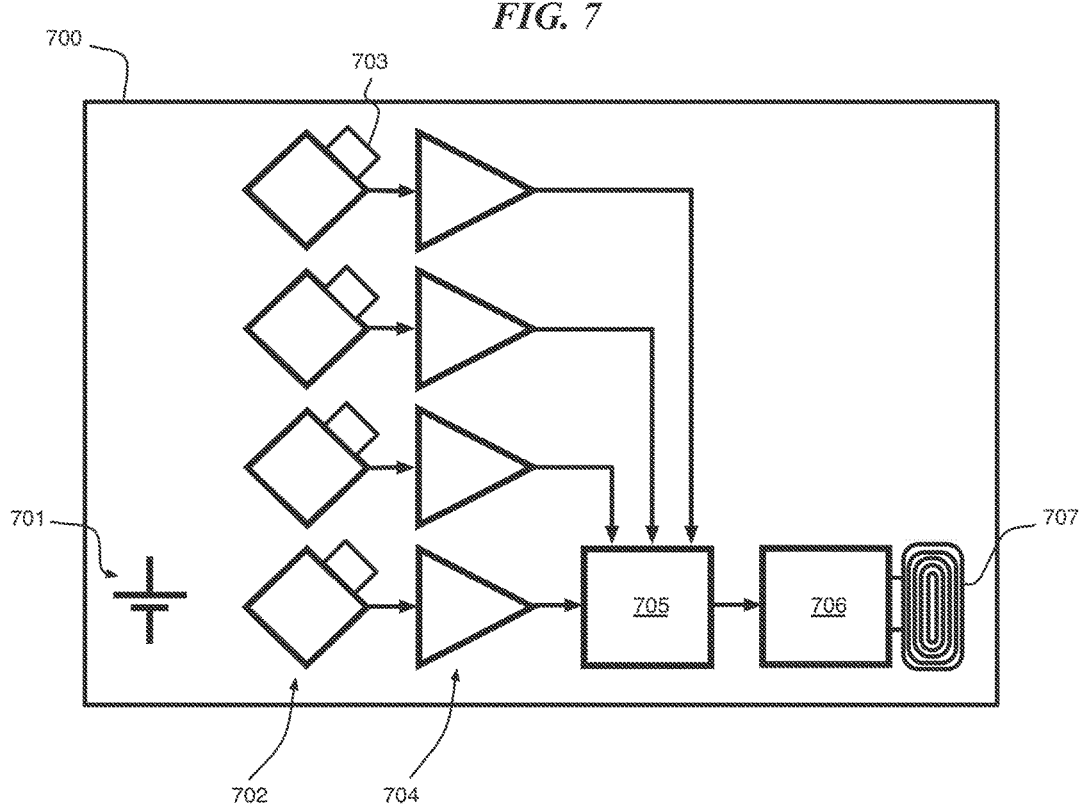
FIG. 7 is a block diagram of a sensor having multiple bridge circuits according to an embodiment of the present invention.

FIG. 7 is a block diagram of a sensor 700 according to an embodiment of the present invention including a power supply 701, a plurality of bridge circuits 702 (e.g., Wheatstone bridge circuits), each comprising a strain gauge, e.g., 703. The sensor 700 further includes amplifier circuits 704 amplifying a voltage signal output by the Wheatstone bridge circuits 702 to generate an amplified signal, an analog-to-digital (A/D) converter 705 converting the amplified signals into a digital signal, a communications controller 706 receiving the digital signal and facilitating communication with a receiver e.g., 500, and the antenna 707 configured to transmit the digital signal. According to an exemplary embodiment of the present invention, the sensor of FIG. 7 can be modified to support a wireless power supply, similar to FIG. 6A.

Figure 8:
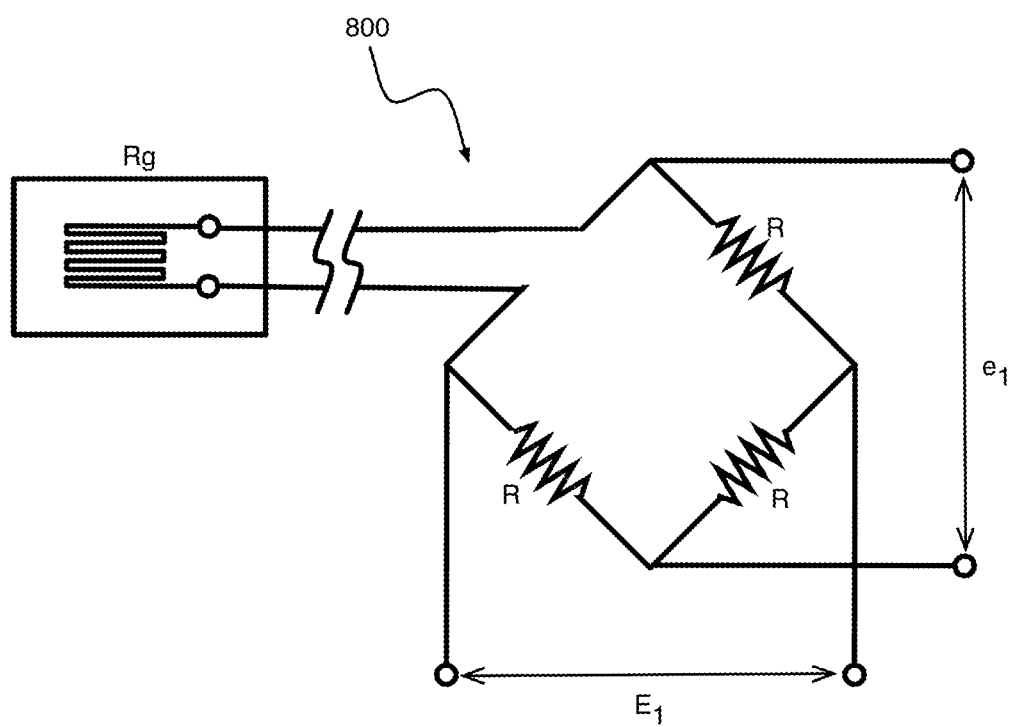
FIG. 8 is a circuit diagram of a bridge circuit according to an embodiment of the present invention.
Figure 9:
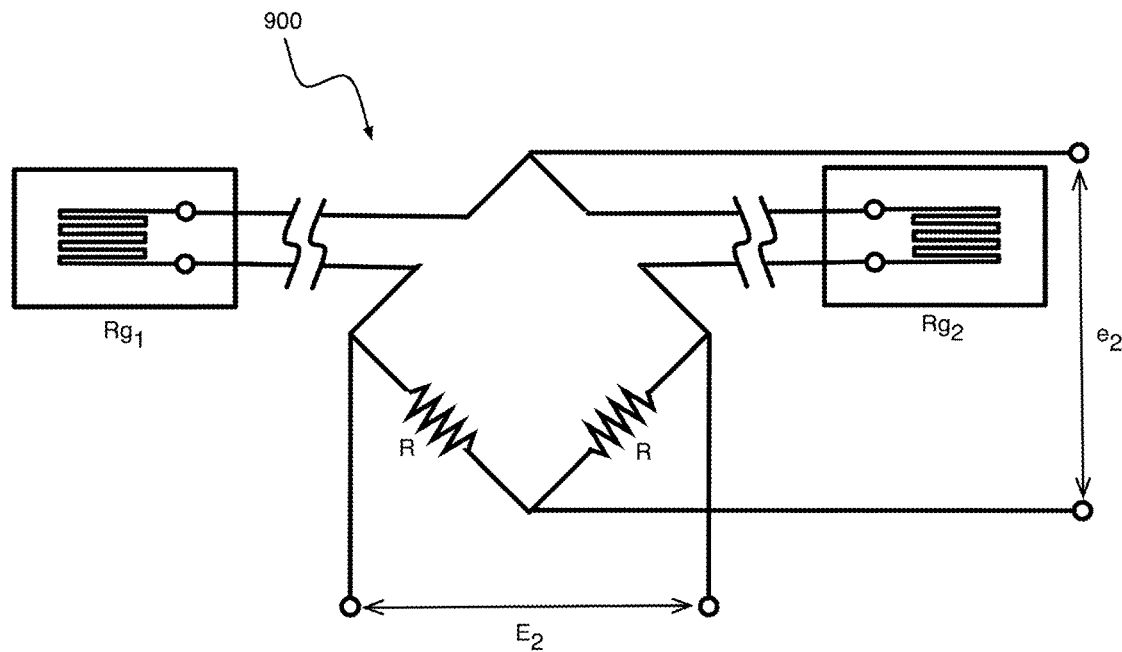
FIG. 9 is a circuit diagram of a bridge circuit according to an embodiment of the present invention.

FIG. 8 and FIG. 9 are circuit diagrams of exemplary bridge circuits, e.g., 402, according to at least one embodiment of the present invention. It should be understood that for any given strain gauge, the gauge factor is a constant. Further, R is a fixed resistance. According to an embodiment of the present invention, in the circuit diagram of FIG. 8, bridge circuit 800 includes strain gauge Rg for measuring a strain related to a voltage output by the following:

$$e_1 = \frac{E_1}{4} K \cdot \varepsilon_1$$

where:
$e_1$ is the voltage output;
$E_1$ is the exciting voltage;
K is a gauge factor; and
$\varepsilon_1$ is the strain of the test piece (e.g., nail plate) measured by the strain gauge Rg.

According to an embodiment of the present invention, in the circuit diagram of FIG. 9, bridge circuit 900 includes a first strain gauge $Rg_1$ and a second strain gauge $Rg_2$. The bridge circuit 900 outputs a signal corresponding to a relative strain measured by the gauges $Rg_1$ and $Rg_2$ using the following:

$$e_2 = K(\varepsilon_1 - \varepsilon_2)\frac{E_2}{4}$$

where:
$e_2$ is the voltage output;
$E_2$ is the exciting voltage;
K is a gauge factor;
$\varepsilon_1$ is the strain of the test piece (e.g., nail plate) measured by the strain gauge $Rg_1$; and
$\varepsilon_2$ is the relative strain of the test piece (e.g., nail plate) measured by the gauge $Rg_2$.

Figure 10:
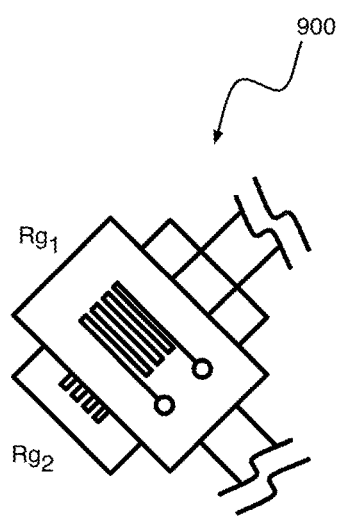
FIG. 10 is a diagram illustrating an exemplary orientation of the strain gauges of FIG. 9 configured as a biaxial sensor, according to an embodiment of the present invention.

The circuit of FIG. 10 is configured in a biaxial sensor 900 having stacked strain gauges $Rg_1$ and $Rg_2$, which is configured to measure nail deformation in two directions. According to one or more embodiments of the present invention, each of the first strain gauge Rg1 and the second strain gauge Rg2 are connected to respective bridge circuits.

Figure 12:
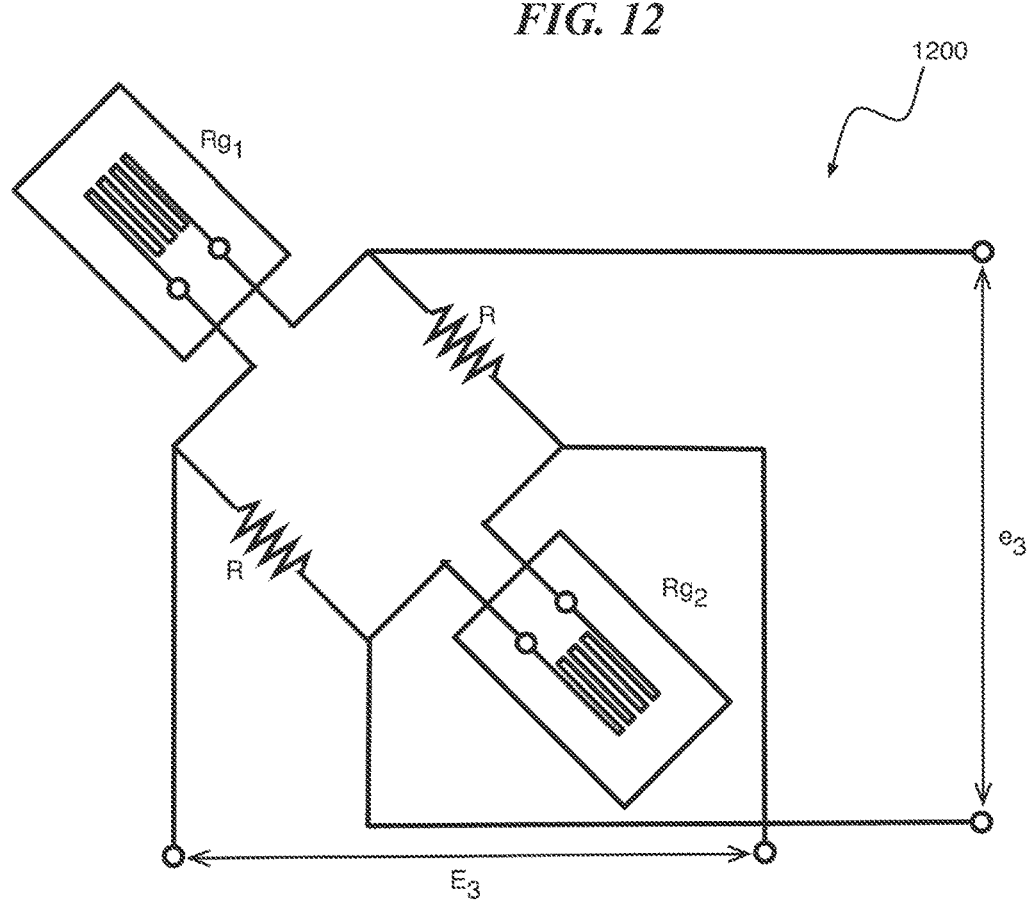
FIG. 12 is a circuit diagram of a bridge circuit for measuring strain according to an embodiment of the present invention.

According to an embodiment of the present invention, the strain gauges Rg1 and Rg2 depicted in FIG. 9 and FIG. 12 can be disposed orthogonal to one another or in other orientations.

Figure 11:
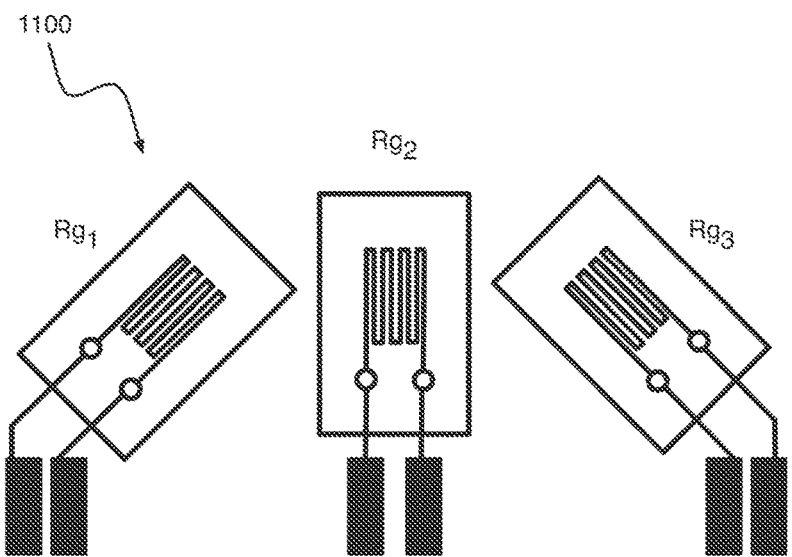
FIG. 11 is a diagram of a plurality of strain gauges disposed according to an embodiment of the present invention.

According to an embodiment of the present invention, FIG. 11 illustrates a configuration 1100 including three strain gauges $Rg_1$, $Rg_2$ and $Rg_3$. In FIG. 11 the strain gauges $Rg_1$ and $Rg_3$ are disposed at an angle of about 60° or less relative to strain gauge $Rg_2$. In a case where the pads of $Rg_1$ and $Rg_3$ are connected to a bridge circuit as shown in FIG. 9, the bridge circuit outputs a signal $Rg_1$-$Rg_3$. In a case where the pads of $Rg_1$ and $Rg_3$ are connected to a bridge circuit as shown in FIG. 12, the bridge circuit outputs a signal $Rg_1$+$Rg_3$. In these two exemplary cases, the pads of $Rg_2$, as depicted in FIG. 11, are connected to a bridge circuit as shown in FIG. 8.

According to an embodiment of the present invention, in the circuit diagram of FIG. 12, bridge circuit 1200 includes a first strain gauge $Rg_1$ and a second strain gauge $Rg_2$ disposed for measuring stress (i.e., tension and compression), using the following:

$$e_3 = K(\varepsilon_1 + \varepsilon_2)\frac{E_3}{4}$$

where:
$e_3$ is the voltage output;
$E_3$ is the exciting voltage;
K is a gauge factor;
$\varepsilon_1$ is the relative strain of the test piece (e.g., nail plate) measured by the gauge $Rg_1$; and
$\varepsilon_2$ is the relative strain of the test piece (e.g., nail plate) measured by the gauge $Rg_2$.

Figure 13:
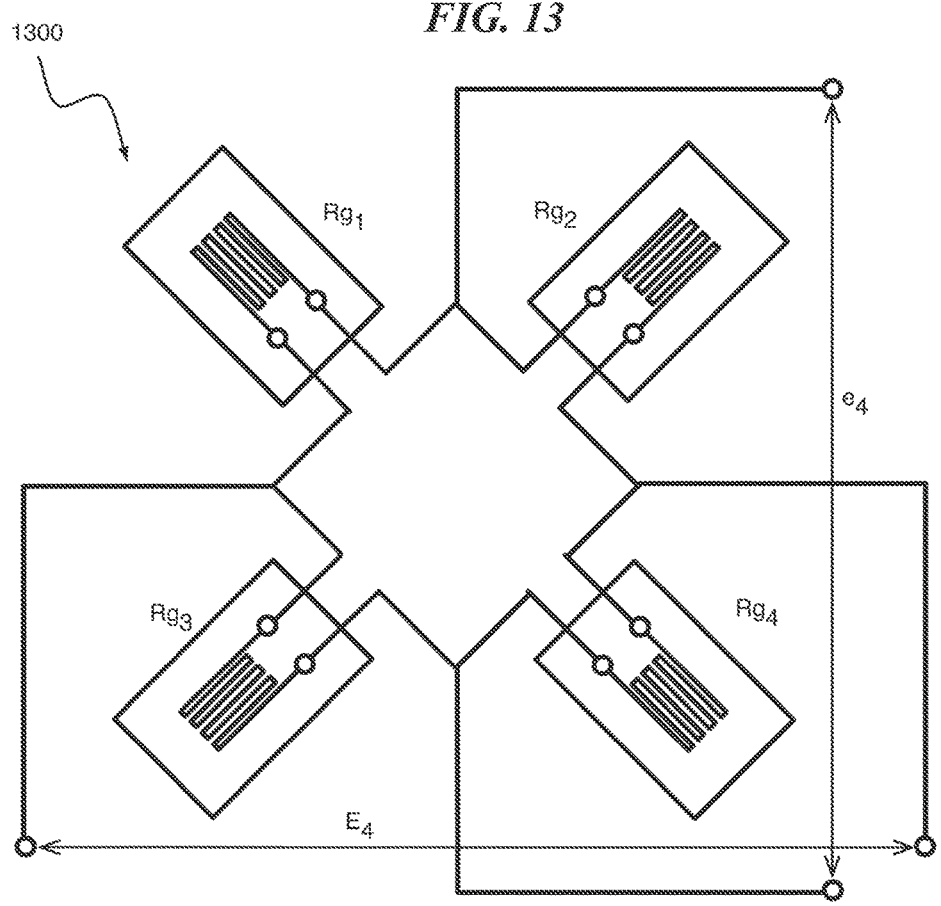
FIG. 13 is a circuit diagram of a bridge circuit according to an embodiment of the present invention.

According to an embodiment of the present invention, in the circuit diagram of FIG. 13, bridge circuit 1300 includes a first strain gauge $Rg_1$, a second strain gauge $Rg_2$, a third strain gauge $Rg_3$, and a fourth strain gauge $Rg_4$ using the following:

$$e_4 = K(\varepsilon_1 - \varepsilon_2 + \varepsilon_3 - \varepsilon_4)\frac{E_4}{4}$$

where:
$e_4$ is the voltage output;
$E_4$ is the exciting voltage;
K is a gauge factor; and
$\varepsilon_1$ is the strain of the test piece (e.g., nail plate 101) measured by the gauge $Rg_1$;
$\varepsilon_2$ is the strain of the test piece (e.g., nail plate 101) measured by the gauge $Rg_2$;
$\varepsilon_3$ is the strain of the test piece (e.g., nail plate 101) measured by the gauge $Rg_3$; and
$\varepsilon_4$ is the strain of the test piece (e.g., nail plate 101) measured by the gauge $Rg_4$.

Figure 14:
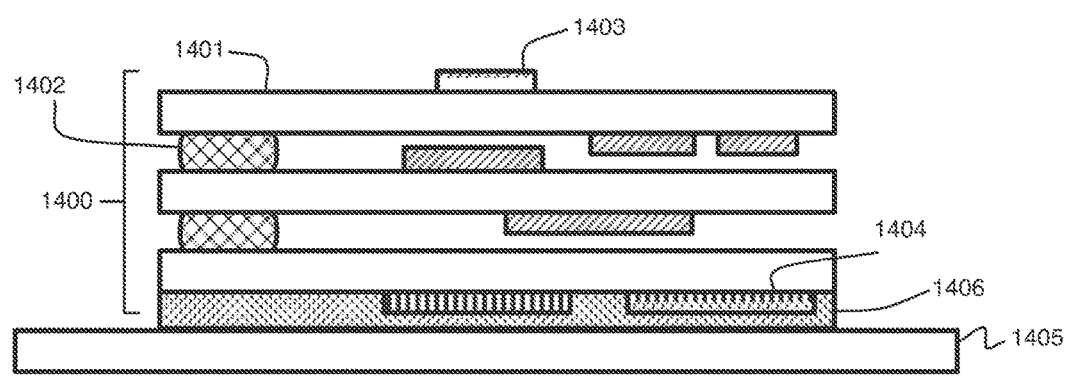
FIG. 14 is a cross-section block diagram of a sensor according to an embodiment of the present invention.
Figure 15:
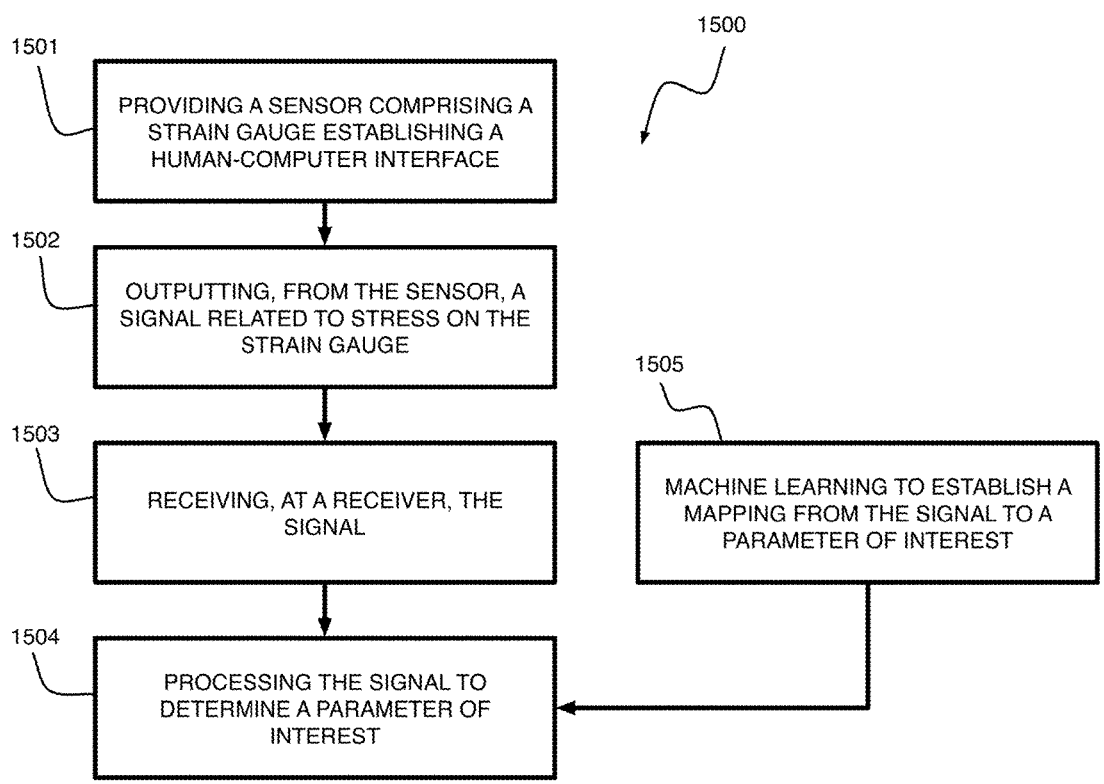
FIG. 15 is a flow diagram of a method of quantifying grip strength and characterizing movement idioms according to an exemplary embodiment of the present invention.

Referring to FIG. 14, a sensor 1400 according to an embodiment of the present invention includes a plurality of printed circuit boards, e.g., 1401, formed as a stack. Adjacent ones of the printed circuit boards are connected by connections 1402 (e.g., solder or sockets). One or more of the printed circuit boards includes an integrated circuit or component 1403, which can be a power supply, bridge circuit, an amplifier circuit, etc. The sensor 1400 further includes one or more strain gauge 1404 disposed on an outward surface of the sensor 1400, wherein the strain gauge 1404 can be disposed facing a substrate 1405 such as a nail plate. The sensor 1400 is attached to the substrate 1405 using an adhesive 1406 such as a glue, double faced tape, etc.

According to one or more embodiments of the present invention, a method 1500 of quantifying grip strength and characterizing movement idioms includes providing a sensor comprising one or more strain gauges establishing a human-computer interface with a subject's nail plate 1501, outputting, by the sensor, a signal related to stress on the strain gauge 1502, receiving, at a receiver, the signal output by the sensor 1503, and processing the signal to determining a parameter of interest 1504. According to one or more embodiments of the present invention, the parameter of interest is one of grip strength and a characterization of a movement idiom, which can be used in determining one or more further parameters, such as an ON or OFF state. It should be understood that the parameters described herein are exemplary, and that one of ordinary skill in the art would recognize that additional parameters can be mapped to the signal output by the sensor.

According to one or more embodiments of the present invention, the method further includes a machine learning process 1505, which establishes for the sensor, a mapping from the signal (e.g., a waveform signal) to a parameter of interest 1504. The mapping is used in processing the signal at 1504. For example, the output of the sensor can be instrumented to determine that a given waveform corresponds to certain grip strength for movement idiom.

According to one or more embodiments of the present invention, the machine learning process 1505 and signal processing 1504 are adapted to an application, e.g., grip force measurement, character and gesture recognition, etc.

According to an embodiment of the present invention, for grip force measurements, the machine learning 1505 includes a training session with a hand dynamometer and sensors yielding finger nail strain measurements and corresponding grip force measurements. The machine learning process 1505 further includes an estimation of a piece-wise linear regression model from the finger nail strain measurements and grip force measurements. Given the piece-wise linear regression model (i.e., 1505), the signal processing 1504 inputting the signal into the model to predict a parameter of interest, in this exemplary case, a grip force of the subject. According to an embodiment of the present invention, the signal processing 1504 comprises grouping/clustering the received strain signals (see block 1503) into idioms. The signal processing 1504 includes recording strain signals over time (e.g., at different visits to a physician or technician, when in wireless communications range of a receiver, etc.), wherein a strain is observed for one or more of the idioms, and is compared over time. This comparison can be of a parameter of interest, such as grip force, and in one or more embodiments, yields outputs such as a maximum grip force, average grip force, a duration of a strain, speed of a grip force activation, etc.

According to one or more embodiments of the present invention, for character and gesture detection, the machine learning 1505 includes training sessions with multiple subjects yielding nail strain measurements for known characters or gestures (for example, a subject uses their figure to trace a character or make a gesture on a surface and a sensor records a strain measurement). Given the strain measurements and the known character tracing or gestures, the machine learning 1505 includes grouping the strain measurements corresponding to the known characters and/or gesture actions, applying dynamic time warping (DTW), and identifying idioms. DTW is a method of measuring the similarity between two temporal sequences that vary in speed. In one or more embodiments of the present invention, a DTW method is applied to compensate for variability (e.g., different subjects doing things at different speeds), wherein the DTW outputs a set of aligned strain measurements. The machine learning 1505 further includes generating a classifier (e.g., k-nearest neighbors, support vector machines (SVM), neural networks, etc.) trained using the strain measurements mapped to character and gesture labels. According to an embodiment of the present invention, the signal processing 1504 includes receiving signals from the sensor and predicting characters and/or gestures from the received signals using the classifier.

According to an embodiment of the present invention, a method of tracking progression of a disease in a subject includes mounting at least one sensor to a nail plate of the subject, measuring, using a sensor, strain on the nail plate to output a data stream, communicating the data stream to a receiver, and interpreting, by the receiver, the data stream to determine a state of the subject.

According to an embodiment of the present invention a wire-based communication implementation is contemplated, wherein the sensor including one or more strain gauges is physically connected to the receiver, for example, by a wire.

According to an embodiment of the present invention, a sensor can be used as an input device of a computer system. For example, passwords are typically restricted to sets of characters that can be guessed and enumerated with brute force methods. Pass-Movements, as measured by a sensor according to an embodiment of the present invention, can be recorded from directional movements, tapping, squeezing, rhythmic motions, etc., and related to a subject's physiognomy. Advantageously a pass-movement recording using a sensor according to an embodiment of the present invention inherently combines the physical characteristics of the subject's finger with finger movement, and can include further measured data such as a time between motions.

The trend to smaller devices, such as smart watches without keyboards or mice, and smaller screens, are constraining options for input. Advantageously, a sensor according to an embodiment of the present invention enables a subject to write on any surface, using the surface as an input device.

Recapitulation:

According to an embodiment of the present invention, the sensor 400 comprises the power supply 401, the bridge circuit 402 powered by the power supply 401 and including one or more strain gauges mounted on a nail plate, the bridge circuit 402 outputting a voltage signal, the amplifier circuit 403 amplifying the voltage signal output by the bridge circuit 402 to generate an amplified signal, the analog-to-digital (A/D) converter 404 converting the amplified signal into a digital signal, the communications controller 405 receiving the digital signal and facilitating communication with a receiver 500, and the antenna 406 configured to transmit the digital signal.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system (e.g., the receiver 500) for characterizing a deformation data stream. Further, a computer program product can include a tangible computer-readable recordable storage medium with code adapted to be executed to carry out one or more method steps described herein, including the provision of the system with the distinct software modules.

Figure 16:
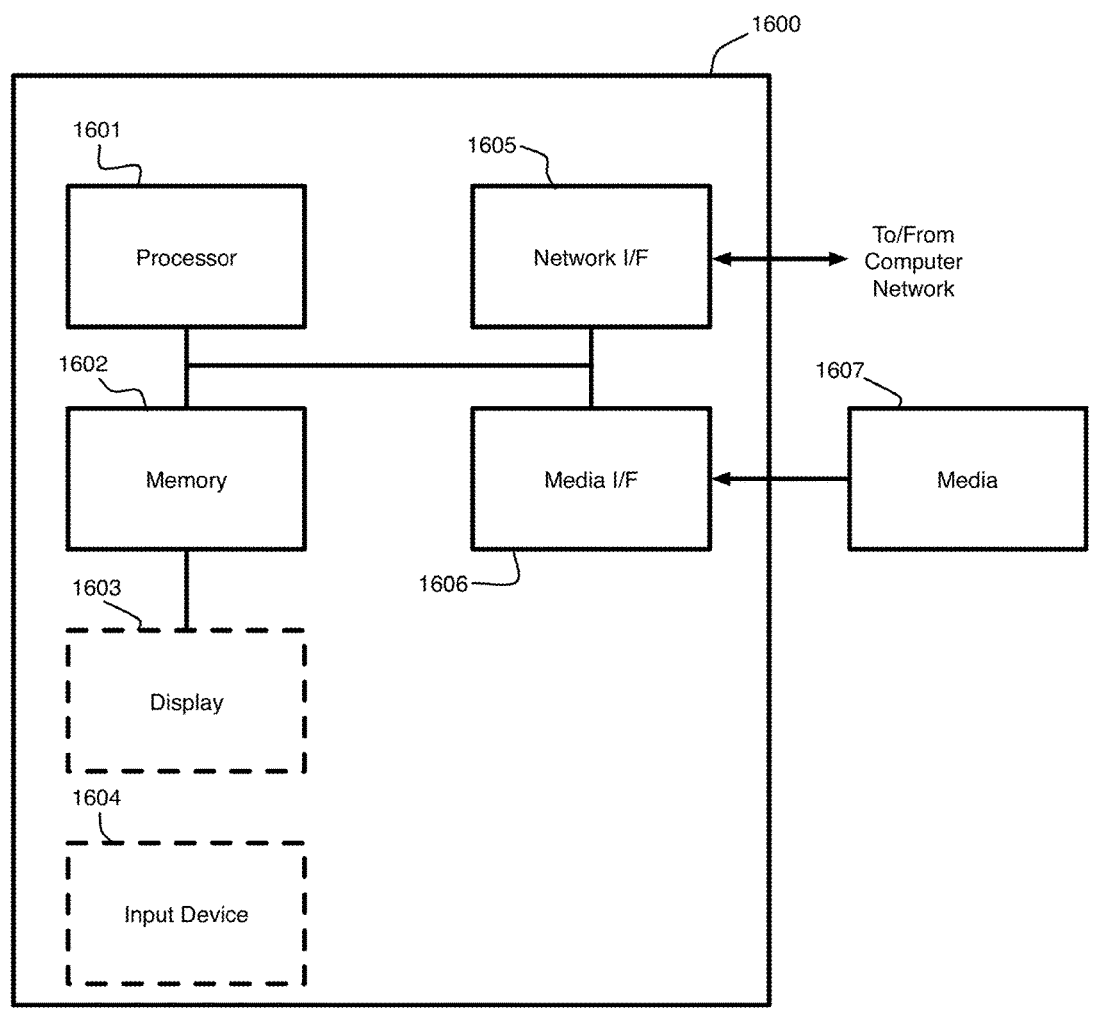
FIG. 16 is a block diagram depicting an exemplary computer system embodying a method of characterizing a deformation data stream for according to an exemplary embodiment of the present invention.

Referring to FIG. 16; FIG. 16 is a block diagram depicting an exemplary computer system embodying the computer system for characterizing a deformation data stream (see receiver 500 in FIG. 5) according to an embodiment of the present invention. The computer system shown in FIG. 16 includes a processor 1601, memory 1602, display 1603, input device 1604 (e.g., keyboard), a network interface (I/F) 1605, a media I/F 1606, and media 1607, such as a signal source, e.g., camera, Hard Drive (HD), external memory device, etc.

In different applications, some of the components shown in FIG. 16 can be omitted. The whole system shown in FIG. 16 is controlled by computer readable instructions, which are generally stored in the media 1607. The software can be downloaded from a network (not shown in the figures), stored in the media 1607. Alternatively, software downloaded from a network can be loaded into the memory 1602 and executed by the processor 1601 so as to complete the function determined by the software.

The processor 1601 may be configured to perform one or more methodologies described in the present disclosure, illustrative embodiments of which are shown in the above figures and described herein. Embodiments of the present invention can be implemented as a routine that is stored in memory 1602 and executed by the processor 1601 to process the signal from the media 1607. As such, the computer system is a general-purpose computer system that becomes a specific purpose computer system when executing routines of the present disclosure.

Although the computer system described in FIG. 16 can support methods according to the present disclosure, this system is only one example of a computer system. Those skilled of the art should understand that other computer system designs can be used to implement embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system comprising:
   a sensor configured to measure stress in a nail plate, the sensor comprising:
   a bridge circuit including one or more strain gauges mounted directly on a flexible circuit board, the one or more strain gauges comprising respective surfaces facing the nail plate, the bridge circuit outputting a voltage signal;
   an amplifier circuit mounted on a second circuit board and amplifying the voltage signal output by the bridge circuit to generate an amplified signal;
   an analog-to-digital (A/D) converter mounted on the second circuit board and converting the amplified signal into a digital signal;
   a controller mounted on the second circuit board and receiving the digital signal and facilitating communication with a receiver;
   an antenna mounted on the second circuit board and configured to transmit the digital signal; and
   a communications bus connecting the flexible circuit board to the second circuit board, wherein the second circuit board is flexible and stacked on a first side of the flexible circuit board, wherein the one or more strain gauges are disposed on a second side of the flexible circuit board opposite the first side, wherein the sensor conforms to a shape of the nail plate, and the communications bus connects respective ends of the second circuit board and the flexible circuit board.

2. The system of claim 1, wherein the bridge circuit comprises:
   a pair of first strain gauges configured to capture strain in a first direction; and
   a pair of second strain gauges configured to capture strain in a second direction different than the first direction.

3. The system of claim 2, the receiver comprising a processor processing the digital signal into a parameter associated with stress in the nail plate.

4. The system of claim 3, wherein the processor processes the digital signal using a mapping associated with a configuration of the first and second strain gauges of the sensor to determine a force applied in the first direction according to changes in the digital signal corresponding to outputs of the first strain gauges and determine a force applied in the second direction according to changes in the digital signal corresponding to outputs of the second strain gauges.

5. The system of claim 1, wherein the bridge circuit comprises:
   a pair of first strain gauges configured to capture strain in a first direction; and
   a pair of second strain gauges configured to capture strain in the first direction.

6. The system of claim 1, wherein the antenna converts a signal received from the receiver into an electric current powering the sensor.

7. The system of claim 1, wherein the sensor further comprises a power supply powering one or more of the bridge circuit, the amplifier circuit, the A/D converter, the controller and the antenna.

8. The system of claim 1, wherein the controller is a communications controller.

9. The system of claim 1, wherein the controller comprises a micro controller and a communications controller, wherein the micro controller is disposed between the A/D converter and the communications controller.

10. The system of claim 1, further comprising a micro controller, wherein at least one of the amplifier circuit and the A/D converter are implemented as software executed by the micro controller.

* * * * *